(12) United States Patent
Mancini et al.

(10) Patent No.: US 9,344,889 B2
(45) Date of Patent: May 17, 2016

(54) METHODS, SYSTEMS AND APPARATUS TO PAIR MEDICAL DEVICES TO AN IN-BODY NETWORK

(71) Applicant: Intel Corporation, Santa Clara, CA (US)

(72) Inventors: Steven A. Mancini, Beaverton, OR (US); Hong Li, El Dorado Hills, CA (US); Igor Tatourian, San Jose, CA (US); Robert L. Vaughn, Portland, OR (US); Tobias M. Kohlenberg, Portland, OR (US); Jesse R. Walker, Portland, OR (US); Esteban Gutierrez, Hillsboro, OR (US); Jim S Baca, Corrales, NM (US); Rita H. Wouhaybi, Portland, OR (US)

(73) Assignee: INTEL CORPORATION, Santa Clara, CA (US)

( * ) Notice: Subject to any disclaimer, the term of this patent is extended or adjusted under 35 U.S.C. 154(b) by 73 days.

(21) Appl. No.: 14/306,723

(22) Filed: Jun. 17, 2014

(65) Prior Publication Data

US 2015/0365826 A1 Dec. 17, 2015

(51) Int. Cl.
| | |
|---|---|
| *H04L 29/06* | (2006.01) |
| *H04W 12/06* | (2009.01) |
| *A61M 5/142* | (2006.01) |
| *H04W 76/02* | (2009.01) |
| *H04W 12/04* | (2009.01) |
| *G06F 19/00* | (2011.01) |

(52) U.S. Cl.
CPC .......... *H04W 12/06* (2013.01); *A61M 5/14276* (2013.01); *G06F 19/3406* (2013.01); *H04W 12/04* (2013.01); *H04W 76/023* (2013.01); *A61M 2205/04* (2013.01); *A61M 2205/3553* (2013.01); *A61M 2205/3561* (2013.01); *A61M 2205/3569* (2013.01); *A61M 2205/3584* (2013.01)

(58) Field of Classification Search
CPC .......... H04L 63/0823; H04L 63/0428
USPC .......... 713/155
See application file for complete search history.

(56) References Cited

U.S. PATENT DOCUMENTS

2010/0061557 A1* 3/2010 Youn ............ H04L 63/062
380/279
2015/0281364 A1* 10/2015 Connolly ............ G06Q 10/06
709/217

OTHER PUBLICATIONS

Sandhana, Lakshmi, "Patients' Own Heartbeat Could Work as Anti-Hacking Password for Implants," Gizmag.com, retrieved from <http://gizmag.com/password-for-medical-implants/29227/>, Sep. 30, 2013 (6 pages).

(Continued)

*Primary Examiner* — Anthony Brown
(74) *Attorney, Agent, or Firm* — Hanley, Flight & Zimmerman, LLC (57) ABSTRACT

Methods, apparatus, systems and articles of manufacture are disclosed to pair devices to an in-body network. An example apparatus disclosed herein includes a device capability manager to identify remote sensors associated with a candidate medical device, an encryption engine to provide the candidate medical device with hashing instructions to be applied to input values from selected ones of the remote sensors, a measurement engine to acquire input values from local sensors corresponding to the selected ones of the available remote sensors during a measurement schedule, the encryption engine to apply the hashing instructions to the input values from the local sensors, and a pairing engine to authorize the candidate medical device when an encryption key associated with the remote sensors includes a threshold indication of parity with an encryption key associated with the local sensors.

20 Claims, 7 Drawing Sheets

(56) References Cited

OTHER PUBLICATIONS

Dodis et al., "Fuzzy Extractors: How to Generate Strong Keys From Biometrics and Other Noisy Data," SIAM Journal on Computing, Jan. 20, 2008 (47 pages).

Paul et al., "A Review of the Security of Insulin Pump Infusion Systems," Journal of Diabetes Science and Technology, Nov. 2011 (15 pages).

Coxworth, Ben, "Wireless Chips and Probes Could Monitor Orthopedic Implants," Gizmag.com, retrieved from <http://www.gizmag.com/ortho-tag-chips-and-probes-for-implants/18901/>, Jun. 13, 2011 (3 pages).

* cited by examiner

METHODS, SYSTEMS AND APPARATUS TO PAIR MEDICAL DEVICES TO AN IN-BODY NETWORK

FIELD OF THE DISCLOSURE

This disclosure relates generally to medical device security and, more particularly, to methods and apparatus to pair medical devices to an in-body network.

BACKGROUND

In recent years, medical devices have become a ubiquitous aspect of the human experience. Such medical devices are typically surgically implanted in a body (e.g., human, animal) to perform various tasks, such as delivery of therapeutic agents (e.g., anti-inflammatory agents, anesthetic agents, anti-coagulants, etc.), organ monitoring (e.g., cardiac monitoring devices, etc.) and organ control (e.g., cardiac resynchronization devices, defibrillator devices, etc.). In some cases, two or more medical devices may be implanted within a single body.

DETAILED DESCRIPTION

An embedded medical device may facilitate a specific purpose to address one or more medical needs of a host body (e.g., human, animal) at a first time. In some examples, one or more additional embedded medical device(s) may be implanted (e.g., surgically implanted) at a second time due to additional/alternate medical needs of the host body. For example, an embedded insulin pump may be surgically implanted into the host body to replicate the function of a failing pancreas and/or help with the effects of diabetes to control a level of glucose in the blood of the host body. In operation, a patient (e.g., the host body) may manually assess a glucose level of the blood (e.g., a home blood test kit) and invoke the embedded pump via remote control (e.g., a wireless remote) when needed. However, in the event that the patient is not competent and/or otherwise unqualified to properly monitor glucose levels of the blood (e.g., patients having dementia, elderly patients, etc.), then a separate and subsequent embedded glucose monitor may be implanted into the patient to measure glucose levels and control the corresponding insulin pump, as needed.

Continuing with the example above, prior to the glucose monitor being able to communicate with the insulin pump, the devices must be paired together on a communication network (e.g., an in-body communication network). Traditionally, the first device implanted into the body needed to be programmed and/or otherwise configured to have prior knowledge of encryption key(s) to allow one or more additional/subsequent devices to communicate therewith. Encryption key(s) are deemed necessary in view of historical acts of willful harm to consumers (e.g., pain-reliever bottles contaminated with cyanide) and demonstrated medical device vulnerabilities (e.g., wireless hacking and control of insulin pumps demonstrated at the McAfee FOCUS 11 conference, October 2011). At least one risk associated with using a predetermined encryption key is that unauthorized access external to the body can occur if an attacker gains knowledge of that key.

Example methods, systems, apparatus and articles of manufacture disclosed herein facilitate pairing of added medical devices to establish or join an existing in-body medical device network using encryption keys derived from internal body characteristics. In other words, rather than expose one or more embedded medical devices to improper/unauthorized access by entities external to the body, examples disclosed herein permit device pairing without the use of predetermined encryption keys and/or keys that require prior knowledge and/or storage by any participating embedded medical device(s) within a body network of a patient. Authorization (e.g., encryption keys) generated and/or otherwise confirmed by examples disclosed herein are a result of only in-body characteristics, thereby reducing (e.g., minimizing) opportunities of improper control over the example embedded devices. Further, leveraging dynamic biometric data that is not available with a similar granularity outside the body bolsters aspects of security associated with embedded medical devices. Examples disclosed herein also eliminate a need to trust an external authority when authorizing an embedded medical device for in-body communication with other embedded device(s).

Figure 1:
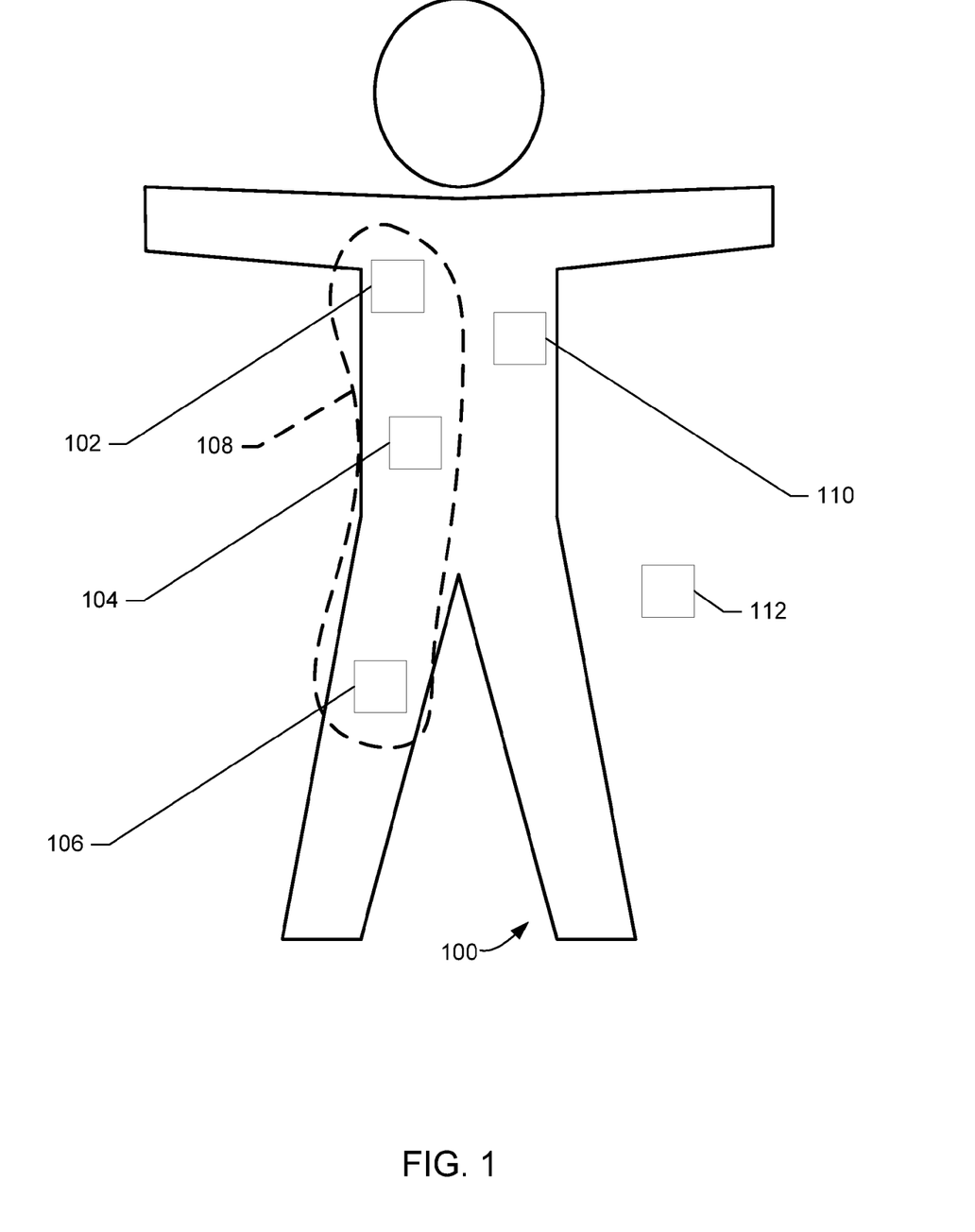
FIG. 1 is a schematic illustration of an example environment having paired medical devices embedded in a host body and a candidate medical device to be added to an in-body network.

FIG. 1 is a schematic illustration of an example patient/body 100 having a first embedded device 102, a second embedded device 104 and a third embedded device 106. Each of the first embedded device 102, the second embedded device 104 and the third embedded device 106 communicate via an in-body network 108 using any type of communication protocol. Because each of the example embedded devices 102, 104, 106 are paired with each other to communicate on the example in-body network 108, subsequent references thereto will be referred to herein as example paired embedded devices 102, 104, 106. Example communication protocols to facilitate inter-device communication in the in-body network 108 include, but are not limited to Internet Protocol Security (IPsec), tcpcrypt, and Transport Layer Security (TLS). While the illustrated example of FIG. 1 includes three embedded devices, example methods, systems, apparatus and/or articles of manufacture disclosed herein may include any number of embedded devices.

In the illustrated example of FIG. 1, a candidate medical device 110 is embedded into the patient 100, but the candidate medical device 110 has not yet been paired with the in-body network 108. For example, the patient 100 may have recently undergone a surgical procedure to install the candidate medical device 110 to perform one or more services to the body 100. While the newly embedded candidate device 110 is intended to communicatively participate with the example in-body network 108, one or more medical-specific functions of the example device 110 may operate independently of example methods, apparatus, systems and/or articles of manufacture disclosed herein.

In operation, and as described in further detail below, the example candidate medical device 110 will pair with the example in-body network 108 only if one or more encryption key(s) generated by the example candidate medical device 110 match one or more encryption key(s) generated by one or more of the example first paired embedded device 102, the example second paired embedded device 104 and/or the example third paired embedded device 106. Additionally, the example candidate medical device 110 will pair with the example in-body network 108 only if all generated encryption key(s) are based on internal characteristics of the patient 100. For example, an external device 112 will not be permitted and/or otherwise generate suitable encryption key(s) because it is external to the patient 100 and, thus, any encryption key(s) generated by the external device 112 will not be based on internal characteristics of that patient 100.

Figure 2:
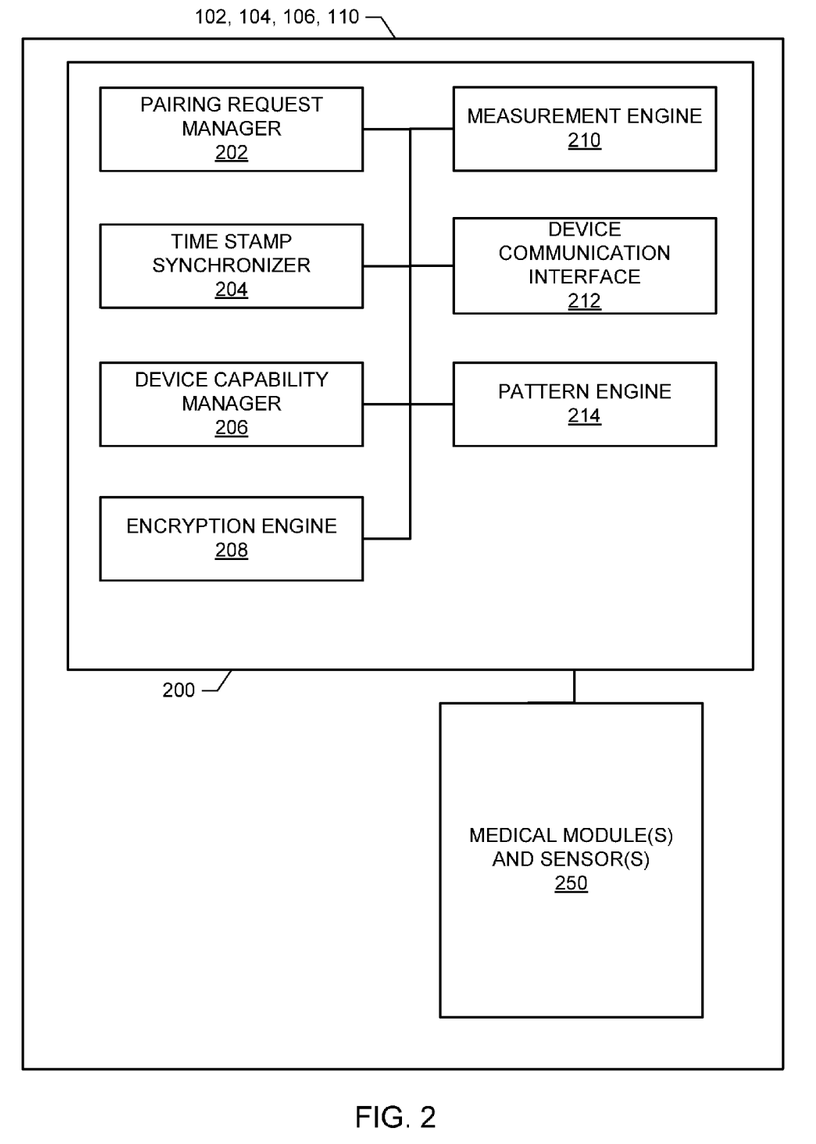
FIG. 2 is a schematic illustration of an example paired medical device or the candidate medical device of FIG. 1.

FIG. 2 is a schematic illustration of an example embedded device 102, 104, 106, 110 as described above in connection with FIG. 1. In particular, the illustrated example of FIG. 2 includes three paired embedded devices (the first paired embedded device 102, the second paired embedded device 104, the third paired embedded device 106) and one unpaired embedded device (the newly embedded candidate device 110). In the illustrated example of FIG. 2, the embedded device (102, 104, 106, 110), whether paired or unpaired, includes a pairing engine 200, a pairing request manager 202, a time stamp synchronizer 204, a device capability manager 206, an encryption engine 208, a measurement engine 210, a device communication interface 212, a pattern engine 214 and medical module(s) and sensor(s) 250. In operation, the example pairing request manager 202 of an example embedded paired device 102 retrieves and/or otherwise receives a pairing request from a requesting device, such as the example embedded candidate device 110. When such a request is obtained, the example time stamp synchronizer 204 of the example embedded paired device 102 sends time synchronization information to the example candidate device 110 to ensure that any datapoints/measurements collected between embedded devices have the same timestamps when data points are collected at the same time. In other words, the example time stamp synchronizer 204 ensures that one or more timing devices in each embedded device (e.g., the paired device 102 and the candidate device 110) are synchronized. As described in further detail below, the candidate device 110 stores the synchronization information so that data collected by the candidate device 110 includes time stamps having parity with time stamped data collected by the example paired embedded device 102.

Because newly added embedded medical devices, such as the example candidate device 110, may include alternate and/or additional functionality, sensors and/or features as compared to the example paired embedded devices (e.g., the example paired embedded device 102), the example device capability manager 206 sends a request to the example candidate device 110 for available sensor types of the candidate device 110. Generally speaking, the example pairing engine 200 may operate in any type of embedded medical device having medical module(s) and sensor(s) 250 that are designed for one or more specific medical needs of the patient 100. In some examples, embedded devices dispense anti-inflammatory agents, anesthetic agents, anti-coagulants and/or insulin. In still other examples, one or more sensors 250 analyze the host body 100 to determine when one or more actions should occur, such as dispensing one or more agents. In some examples, embedded devices initiate life-saving organ control actions, such as cardiac resynchronization signals to a heart of the patient 100, or administering defibrillation signals to the heart in response to sensor 250 detection of heart failure.

Example sensors that embedded devices (102, 104, 106, 110) may use to generate biometric data include, but are not limited to, DNA sequencers, blood type testers, cholesterol testers, glucose testers, blood oxygen testers, blood pH testers, bone density testers, conductivity testers (e.g. between points of the body 100), hormone level testers, blood flow rate testers, accelerometers, vibration sensors, blood pressure sensors, etc. In some examples disclosed in further detail below, sensor rate values of change over time offer additional indications of authenticity. After obtaining information from the example candidate device 110 regarding available sensors, the example device capability manager 206 of the paired embedded device 102 sends a selection to the candidate device 110 regarding which sensor(s) are to be used for authentication. In some examples, the selection of sensors may be chosen randomly by the paired embedded device 102, as long as such random selection of sensors are available at both the paired embedded device 102 and the example candidate embedded device 110. The example device capability manager 206 of the example paired embedded device 102 may also send instructions to the example candidate device 110 regarding a particular sample rate and/or quantity of measurements to be taken during one or more authentication attempts.

As described above, rather than storing predetermined encryption keys in each embedded device to be used for authentication purposes, example methods, apparatus, systems and/or articles of manufacture disclosed herein employ in-body characteristics of the patient to generate encryption keys. At least one example benefit of employing in-body characteristics for generating encryption keys is that the embedded devices do not contain predetermined stored encryption keys in one or more memory devices that may be susceptible to hacking discovery activity. In operation, the example embedded paired device 102 invokes the example sensors 250 to capture in-body characteristics as input to one or more hashing algorithms. Each measurement from the example sensors 250 is associated with a time stamp. Additionally, the example embedded paired device 102 instructs the candidate device 110 to also take measurement(s) at substantially the same time with its sensors, which are also associated with time stamps. The example encryption engine 208 of the embedded paired device 102 provides the candidate embedded device 110 with the same encryption instructions used by the paired device 102. Because both the embedded paired device 102 and the candidate embedded device 110 generate encryption key(s) using the same encryption algorithm(s) at substantially the same time, resulting encryption key(s) therebetween may be compared to determine a degree of similarity. If the degree of similarity is within a threshold value, then the candidate device 110 may be deemed authenticated and paired with the example in-body network 108.

Hashing instructions provided by the example encryption engine 208 of the paired device 102 to a corresponding encryption engine of the example candidate device 110 may be of any type. In some examples, converting biometric information into one or more encryption keys are accomplished in a manner consistent with Fuzzy Extractors: How to Generate Strong Keys from Biometrics and Other Noisy Data, Dodis et al., published on Jan. 20, 2008, the contents of which are incorporated by reference herein in its entirety.

In some examples, the example pattern engine 214 applies a pattern analysis to measured biometric information. For example, the paired embedded device 102 may invoke a glucose sensor to acquire blood sugar measurements during generally established meal times and identify threshold changes in blood sugar values indicative of food consumption. Additionally, before authentication of the candidate embedded device 110, the same or similar measurement values may be acquired by the sensors associated therewith. A potential hacker would need to know several aspects of the authentication process that are neither predetermined nor available to an environment external to the body 100. For example, the hacker would need to know: what type of biometric sensor(s) are employed and/or otherwise negotiated for the authentication process; what times (e.g., times of day) measurements are taken; negotiated time synchronization information; and duplicate in-body characteristics that have a threshold degree of similarity with the example embedded paired device 102.

While an example manner of implementing the embedded device 102, 104, 106, 110 of FIGS. 1 and 2 is illustrated in FIG. 2, one or more of the elements, processes and/or devices illustrated in FIG. 2 may be combined, divided, re-arranged, omitted, eliminated and/or implemented in any other way. Further, the example embedded device 102, 104, 106, 110, the example pairing request manager 202, the example time stamp synchronizer 204, the example device capability manager 206, the example encryption engine 208, the example measurement engine 210, the example device communication interface 212, the example pattern engine 214, the example sensors 250 and/or, more generally, the example pairing engine 200 of FIG. 2 may be implemented by hardware, software, firmware and/or any combination of hardware, software and/or firmware. Thus, for example, any of the example embedded device 102, 104, 106, 110, the example pairing request manager 202, the example time stamp synchronizer 204, the example device capability manager 206, the example encryption engine 208, the example measurement engine 210, the example device communication interface 212, the example pattern engine 214, the example sensors 250 and/or, more generally, the example pairing engine 200 of FIG. 2 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example embedded device 102, 104, 106, 110, the example pairing request manager 202, the example time stamp synchronizer 204, the example device capability manager 206, the example encryption engine 208, the example measurement engine 210, the example device communication interface 212, the example pattern engine 214, the example sensors 250 and/or, more generally, the example pairing engine 200 of FIG. 2 is/are hereby expressly defined to include a tangible computer readable storage device or storage disk such as a memory, a digital versatile disk (DVD), a compact disk (CD), a Blu-ray disk, etc. storing the software and/or firmware. Further still, the example embedded device 102, 104, 106, 110 of FIGS. 1 and 2 may include one or more elements, processes and/or devices in addition to, or instead of, those illustrated in FIG. 4, and/or may include more than one of any or all of the illustrated elements, processes and devices.

Figure 3A:
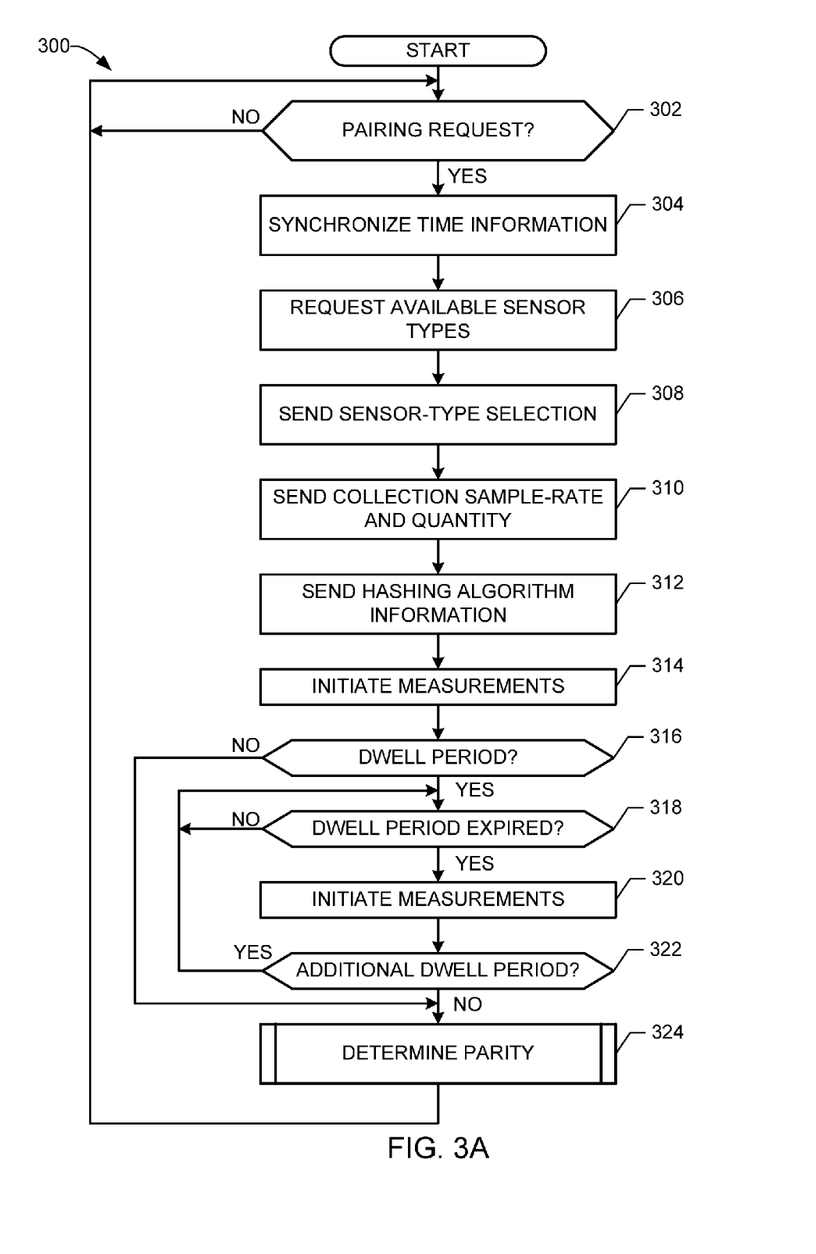
FIGS. 3A and 3B are flowcharts representative of example machine readable instructions that may be executed by the example paired medical devices of FIGS. 1 and 2 to authorize the candidate medical device to participate in the in-body network in a manner consistent with the teachings of this disclosure.
Figure 3B:
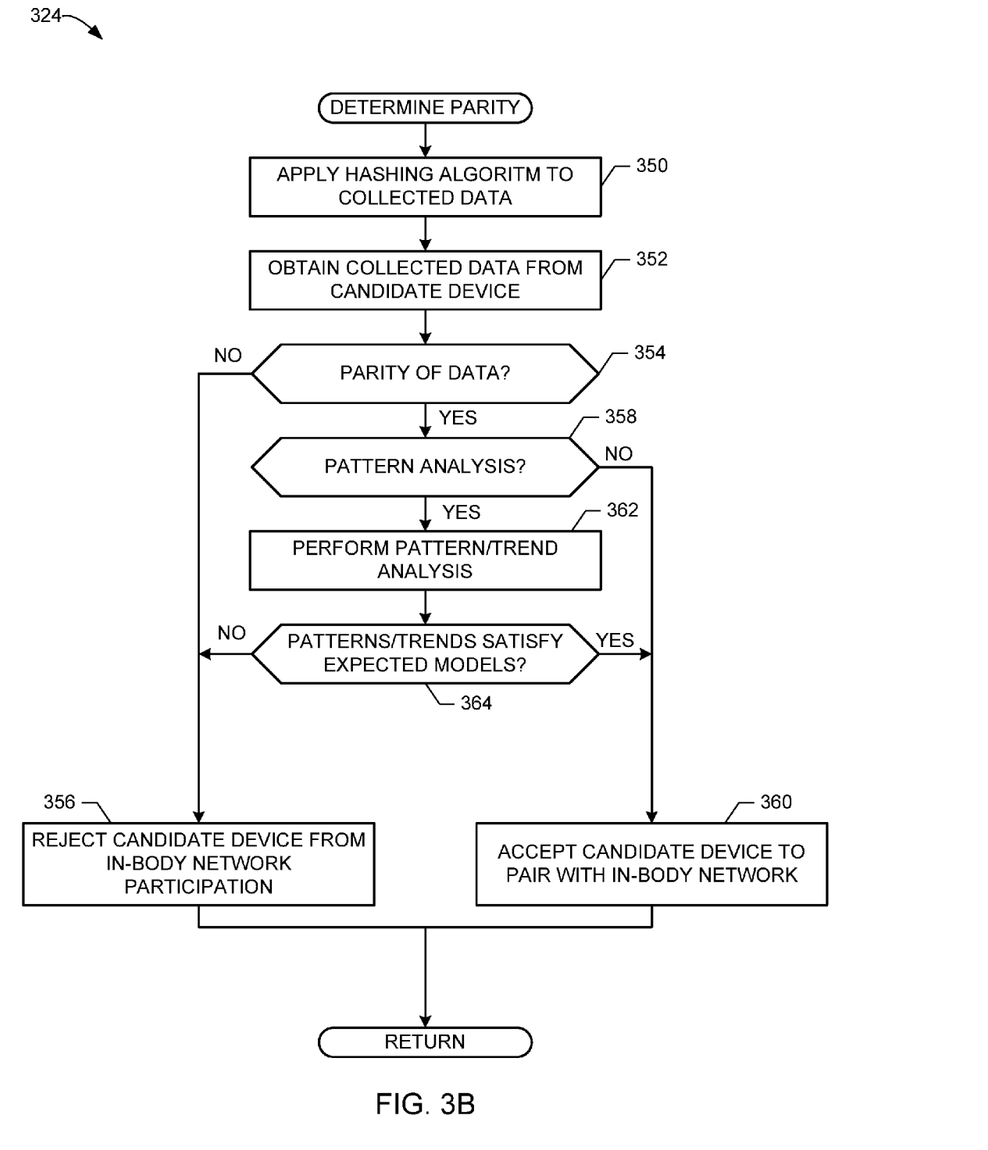
Figure 5:
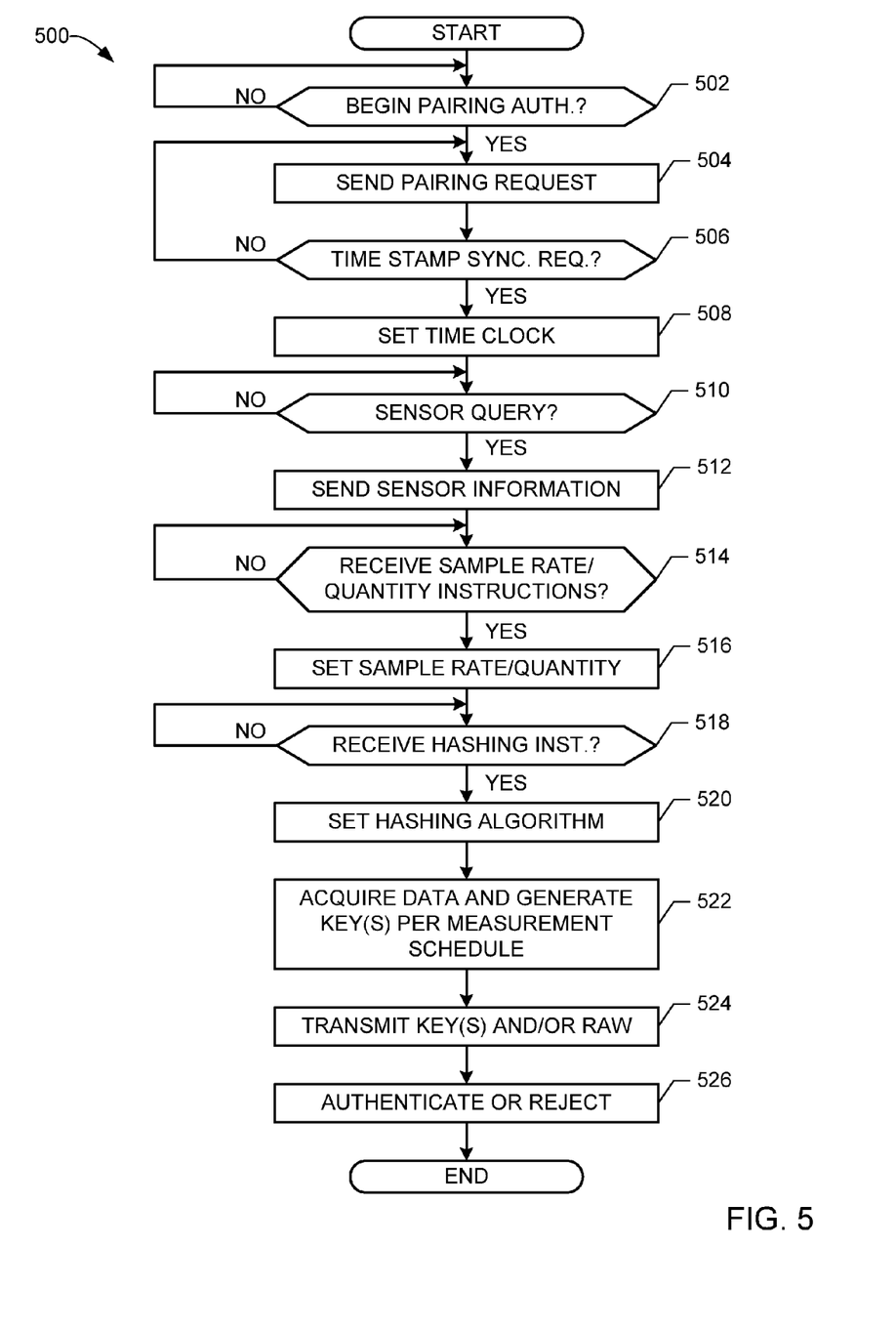
FIG. 5 is a flowchart representative of example machine readable instructions that may be executed by the example candidate medical device of FIGS. 1 and 2 to request authorization to participate in the in-body network in a manner consistent with the teachings of this disclosure.

Flowchart(s) representative of example machine readable instructions for implementing the pairing engine 200 of FIG. 2 is/are shown in FIGS. 3A, 3B and 5. In these examples, the machine readable instructions comprise program(s) for execution by a processor such as the processor 612 shown in the example processor platform 600 discussed below in connection with FIG. 6. The program(s) may be embodied in software stored on a tangible computer readable storage medium such as a CD-ROM, a floppy disk, a hard drive, a digital versatile disk (DVD), a Blu-ray disk, or a memory associated with the processor 612, but the entire program and/or parts thereof could alternatively be executed by a device other than the processor 612 and/or embodied in firmware or dedicated hardware. Further, although the example program(s) is/are described with reference to the flowchart(s) illustrated in FIGS. 3A, 3B and 5, many other methods of implementing the example pairing engine 200 may alternatively be used. For example, the order of execution of the blocks may be changed, and/or some of the blocks described may be changed, eliminated, or combined.

As mentioned above, the example processes of FIGS. 3A, 3B and 5 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 3A, 3B and/or 5 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

The program 300 of FIG. 3A begins at block 302 where the example pairing request manager 202 of an example paired embedded device 102 obtains an indication of a pairing request for the example embedded candidate device 110, which was recently implanted into the example body 100 and is, therefore, currently unpaired. Generally speaking, the program 300 of FIG. 3A reflects operation of the example paired embedded device 102 during one or more attempts to pair a currently unpaired embedded device, such as the example unpaired candidate device 110. In some examples disclosed herein, the paired embedded device 102 is referred to as a host device and the candidate device 110 is referred to as a remote device. If the example pairing request manager 202 does not obtain (e.g., retrieve and/or otherwise receive) the indication of a pairing request (block 302), then the example program 300 of FIG. 3A continues to wait for such an occurrence. On the other hand, in response to obtaining an indication of the pairing request (block 302), the example time stamp synchronizer 204 sends time synchronization information to the device making the pairing request (block 304).

Because the example paired embedded device 102 does not know one or more sensor capabilities of the remote device (i.e., the candidate device 110 making the pairing request), the example device capability manager 206 sends a request to the example unpaired candidate device 110 (block 306). The request allows for identification of available remote sensors of the remote device 110. In response to obtaining information from the example unpaired candidate device 110 regarding what types of sensors it has, the example device capability manager 206 of the example paired embedded device 102 sends configuration instructions regarding which available sensors should be used during the pairing process (block 308). The example device capability manager 206 also sends configuration instructions to the candidate device 110 regarding a particular sensor measurement sample rate and/or sample measurement quantity (block 310).

As described above, example methods, apparatus, systems and/or articles of manufacture disclosed herein improve medical device security by eliminating a need to store predetermined encryption keys within a memory. Instead, examples disclosed herein generate one or more encryption keys only after a medical device is embedded within the example body 100, and such one or more encryption keys are generated based on input from characteristics only available internal to the example body 100. The example encryption engine 208 of the example paired embedded device 102 sends hashing algorithm configuration instructions to the candidate device 110 (block 312). As described above, any type of hashing algorithms may be instructively used by the example paired embedded device 102 and/or unpaired candidate device 110 when generating encryption keys. In some examples, key generation may be performed in a manner consistent with Fuzzy Extractors: How to Generate Strong Keys from Biometrics and Other Noisy Data, Dodis et al., published on Jan. 20, 2008, the contents of which are incorporated by reference herein in its entirety.

The example measurement engine 210 of the example paired device 102 initiates a one or more measurements using the example sensors 250 (local sensors) based on a measurement schedule (block 314). Measurements initiated and/or otherwise invoked by the example measurement engine 210 of the example paired device 102 may occur during scheduled times or in a periodic manner. As described above in connection with block 310, the example measurement engine also sends the measurement schedule to the example unpaired candidate device 110 so that both embedded devices (i.e., the example paired embedded device 102 and the example unpaired candidate embedded device 110) capture measurement data at substantially the same time. For example, the measurement schedule generated by the measurement engine 210 may require a particular number of sensor 250 samples to be acquired once every particular time duration (e.g., ten samples every sixty minutes). Because the example measurement schedule of the paired device 102 is also shared with the example unpaired candidate device 110, both devices will acquire the same number of sensor measurements having substantially same time stamps. As such, any attempts to spoof and/or otherwise fake readings by an unauthorized device external to the body (e.g., the example external device 112) will require relatively precise and scheduled measurements that will be difficult for an attacker to duplicate outside the example body 100.

In the event the example measurement schedule invoked by the example measurement engine 210 includes one or more iterations of sensor 250 measurements, a dwell period is invoked in between each iteration (block 316). The example measurement engine 210 determines whether the dwell period ends (block 318) and, if so, the example measurement engine 210 initiates another iteration of sensor 250 measurements (block 320). If one or more additional dwell periods are part of the example measurement schedule (block 322), then control returns to block 318 to determine when the next dwell period expires. However, if no further measurement iterations are to occur (e.g., no further dwell periods) (block 322), or if the example measurement engine 210 only invoked a single sensor 250 measurement (block 316), then the example pairing engine 200 determines a degree of parity collected by the example paired embedded device 102 (block 324), as described in further detail below.

FIG. 3B illustrates additional detail to determine a degree of parity collected by the example paired embedded device 102 with the candidate embedded device 110. In the illustrated example of FIG. 3B, the example encryption engine 208 applies a hashing algorithm to the collected sensor 250 data to generate one or more encryption key value(s) (block 350). Additionally, because the candidate embedded device 110 has been configured to invoke its own sensors using the same data acquisition rate and number of measurement iteration(s), the example device communication interface 212 obtains measurement data from the example candidate embedded device 110 for comparison purposes (block 352). In some examples, the device communication interface 212 obtains encryption keys generated by the candidate embedded device 110 that were generated using the same hashing algorithm as the encryption engine 208 of the paired embedded device 102. Additionally or alternatively, the example device communication interface 212 obtains raw sensor measurement values captured by the example candidate device 110 for pattern analysis, as described in further detail below.

In the event the example encryption engine 208 of the paired embedded device 102 compares the encryption key obtained from the example candidate device 110 and determines a difference, a threshold difference or other indication of a lack of parity and/or a threshold degree of parity therebetween (block 354), then the example candidate device is rejected and/or otherwise blocked from pairing with the in-body network 108 (block 356). In some examples, the time stamp synchronizer verifies that time stamp values are the same between the paired device 102 and the candidate device 110 as another indication of authenticity. In the event the time stamps associated with local sensor 250 data samples differ by a threshold amount when compared to the remote sensor data samples, the example pairing engine 200 may prohibit the candidate device 110 from pairing with the in-body network 108. However, in the event that an indication of parity is true (block 354), then the example pattern engine 214 determines whether further pattern analysis is to be applied to raw sensor measurement values captured by the example candidate device 110 (block 358). If not, then the granting of access for the example candidate device 110 to pair with the example in-body network 108 (block 360) is based on the observed parity between the encryption key(s) generated by the example paired device 102 and the encryption key(s) generated by the example candidate device 110.

As described above, the example pairing engine 200 may invoke the example pattern engine 214 to perform pattern analysis on acquired sensor 250 data (block 362). Despite generating an indication of parity between the paired embedded device 102 and the candidate embedded device 110, one or more additional indications of authenticity may be required before granting access to the in-body network 108. The pattern engine 214 may verify that acquired sensor 250 data is consistent with expected values that are typically exhibited by the host body 100 (e.g., a human body, an animal body, etc.) (block 364). For example, for any given heart rate of the human body, a corresponding blood flow velocity value is expected. In some examples, absolute values for heart rate and corresponding blood flow velocities are not a primary focus, but instead an expected proportional change (e.g., percentage change) of the blood flow velocity as the heart rate increases and/or decreases.

Figure 4:
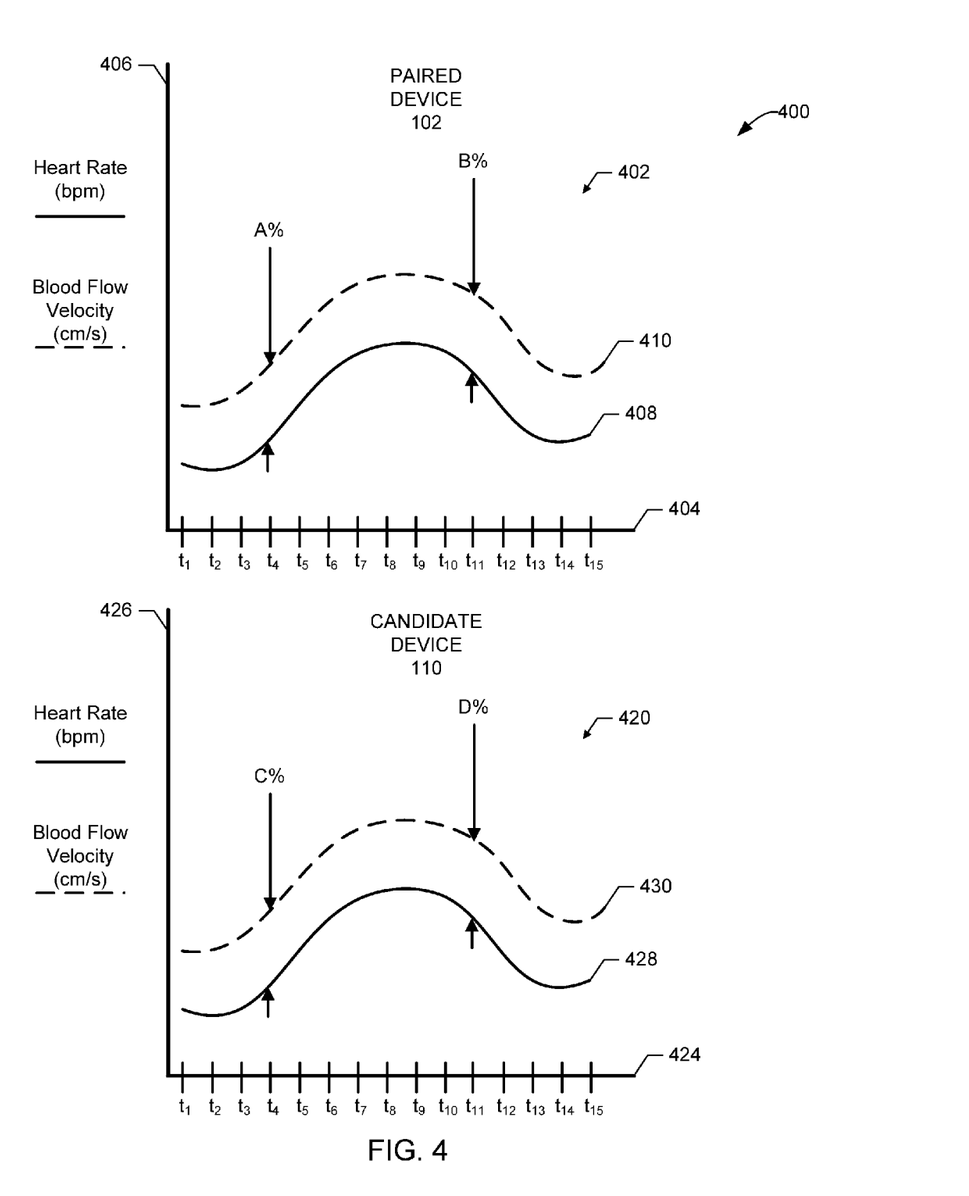
FIG. 4 are example sensor output graphs of acquired sensor data from the example paired medical devices embedded in the host body and the candidate medical device to be added to the in-body network.

FIG. 4 illustrates example sensor output graphs 400 associated with sensor data acquired by the example paired device 102 and sensor data acquired by the example candidate device 110. In the illustrated example of FIG. 4, the paired device graph 402 includes a timestamp axis 404 and a sensor value axis 406. An example heart rate trace 408 reflects acquired heart rate values at corresponding time stamps 404, and an example blood flow velocity trace 410 reflects acquired blood flow velocity values at corresponding time stamps 404. As shown by the example heart rate trace 408 and the example blood flow velocity trace 410, a corresponding difference value is exhibited therebetween at time stamp value $t_4$. In particular, the difference value in the illustrated example of FIG. 4 at time stamp value $t_4$ is shown as a percentage value "A %." Additionally, example time stamp value $t_{11}$ exhibits an example difference value "B %." One or more threshold difference values may be used to compare against A % and B % to determine whether such acquired data points are truly indicative of human physiological responses, thereby reducing the chances that acquired data points are spoofed and/or otherwise compromised.

Similarly, the acquired data from the example candidate device 110 is shown by the candidate device graph 420, which includes a timestamp axis 424 and a sensor value axis 426. An example heart rate trace 428 reflects acquired heart rate values at corresponding time stamps 424, and an example blood flow velocity trace 430 reflects acquired blood flow velocity values at corresponding time stamps 424. As shown by the example heart rate trace 428 and the example blood flow velocity trace 430, a corresponding difference value is exhibited therebetween at time stamp value $t_4$. In particular, the difference value in the illustrated example of FIG. 4 at time stamp value $t_4$ is shown as a percentage value "C %." Additionally, example time stamp value $t_{11}$ exhibits an example difference value "D %." In a manner similar to the example paired device plot 402, one or more threshold difference values may be used to compare against C % and D % to determine and/or otherwise verify whether such acquired data points are truly indicative of human physiological responses. Furthermore, because timestamp t4 of the paired device graph 402 and timestamp t4 of the candidate device graph 420 were each acquired within the same body 100 at the same time, corresponding difference values A % and C % should be within a threshold value of each other as an added measure of verification that the candidate device 110 is installed in the body 100.

The program 500 of FIG. 5 begins at block 502 where the example pairing request manager 202 of the example candidate embedded device 110 transmits or otherwise sends a request to begin pairing authorization. Unlike the example program 300 of FIG. 3A, which reflects a point of view from the example paired device 102, the illustrated example program 500 of FIG. 5 reflects a point of view from the example candidate device 110. Additionally, the example candidate device 110 employs the same pairing engine 200 as is employed by the example paired device 102, but the corresponding sensor(s) and/or medical module(s) 250 of the example candidate device 110 may be different than those of the example paired device 102.

In the illustrated example of FIG. 5, the device communication interface 212 sends the request to begin pairing authorization (block 504), and the time stamp synchronizer 204 awaits a time stamp synchronization request (block 506) so that both the time stamps of the paired device 102 and the candidate device 110 are the same. Upon receipt of the time stamp synchronization information (block 506), the example time stamp synchronizer 204 sets a time clock in a manner that is the same as a time clock associated with the example paired device 102 (block 508). Upon receipt of a request to disclose and/or otherwise share sensor capabilities of sensors 250 associated with the example candidate device 110 by the example device capability manager 206 (block 510), the device communication interface 212 sends sensor availability information to the requesting paired device 102 (block 512).

The example measurement engine 210 awaits for receipt of instructions regarding data acquisition sample rate(s), quantities and or a measurement schedule (block 514) and, once received and/or otherwise obtained from the example paired device 102, the example measurement engine 210 configures the example pairing engine 200 to acquire data in the scheduled manner (block 516). The example encryption engine 208 of the example candidate device 110 awaits for receipt of hashing algorithm instructions (block 518) and, once received, configures the example pairing engine 200 to generate encrypted key(s) in a manner consistent with the received algorithm instructions (block 520).

Based on the obtained measurement schedule from the example paired device 102, the example pairing engine 200 acquires sensor 250 data samples and applies corresponding hashing instructions (block 522). Upon completion of the measurement schedule, the example device communication interface 212 of the candidate device 110 transmits encrypted keys, collected raw data samples, or both (block 524). Based on analysis of the data collected by both the candidate device 110 and the paired device 102 in a manner consistent with examples disclosed above, the example pairing engine 200 of the candidate device 110 receives permission to communicate on the in-body network 108 or is rejected therefrom (block 526).

Figure 6:
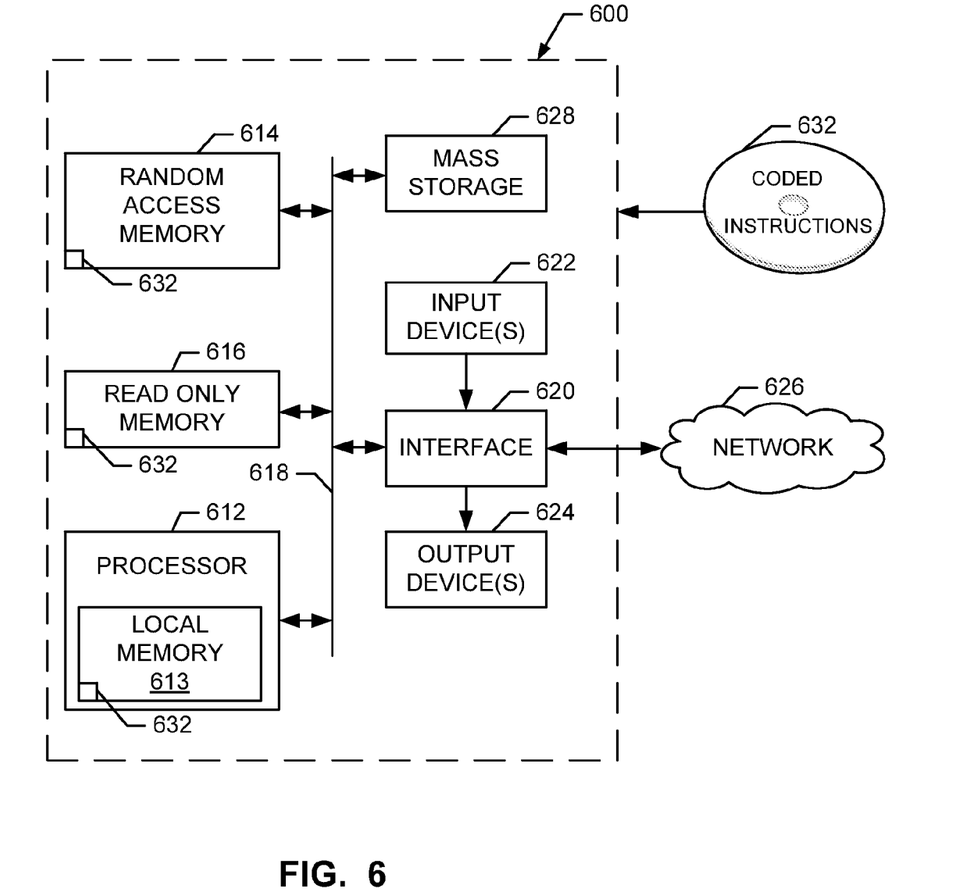
FIG. 6 is a schematic illustration of an example processor platform that may execute the instructions of FIGS. 3A, 3B and 5 to implement the example medical devices of FIGS. 1 and 2.

FIG. 6 is a block diagram of an example processor platform 600 capable of executing the instructions of FIGS. 3A, 3B and 5 to implement the pairing engine 200 of FIG. 2. The processor platform 600 can be, for example, a server, a personal computer, a mobile device (e.g., a cell phone, a smart phone, a tablet such as an iPad™), a personal digital assistant (PDA), an Internet appliance, or any other type of computing device.

The processor platform 600 of the illustrated example includes a processor 612. The processor 612 of the illustrated example is hardware. For example, the processor 612 can be implemented by one or more integrated circuits, logic circuits, microprocessors or controllers from any desired family or manufacturer.

The processor 612 of the illustrated example includes a local memory 613 (e.g., a cache). The processor 612 of the illustrated example is in communication with a main memory including a volatile memory 614 and a non-volatile memory 616 via a bus 618. The volatile memory 614 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 616 may be implemented by flash memory and/or any other desired type of memory device. Access to the main memory 614, 616 is controlled by a memory controller.

The processor platform 600 of the illustrated example also includes an interface circuit 620. The interface circuit 620 may be implemented by any type of interface standard, such as an Ethernet interface, a universal serial bus (USB), and/or a PCI express interface.

In the illustrated example, one or more input devices 622 are connected to the interface circuit 620. The input device(s) 622 permit(s) a user to enter data and commands into the processor 612. The input device(s) can be implemented by, for example, an audio sensor, a microphone, a camera (still or video), a button, a touchscreen, and/or a voice recognition system.

One or more output devices 624 are also connected to the interface circuit 620 of the illustrated example. The output devices 624 can be implemented, for example, by display devices (e.g., a light emitting diode (LED), an organic light emitting diode (OLED), a liquid crystal display, a tactile output device, a light emitting diode (LED), and/or speakers). The interface circuit 620 of the illustrated example, thus, typically includes a graphics driver card, a graphics driver chip or a graphics driver processor.

The interface circuit 620 of the illustrated example also includes a communication device such as a transmitter, a receiver, a transceiver, a modem and/or network interface card to facilitate exchange of data with external machines (e.g., computing devices of any kind) via a network 626 (e.g., an Ethernet connection, a digital subscriber line (DSL), a telephone line, coaxial cable, a cellular telephone system, etc.).

The processor platform 600 of the illustrated example also includes one or more mass storage devices 628 for storing software and/or data. Examples of such mass storage devices 628 include floppy disk drives, hard drive disks, compact disk drives, Blu-ray disk drives, RAID systems, and digital versatile disk (DVD) drives.

The coded instructions 632 of FIGS. 3A, 3B and 5 may be stored in the mass storage device 628, in the volatile memory 614, in the non-volatile memory 616, and/or on a removable tangible computer readable storage medium such as a CD or DVD.

From the foregoing, it will be appreciated that the above disclosed methods, apparatus and articles of manufacture improve security of one or more devices embedded into a body, such as a human body. Additionally, examples disclosed herein avoid the use of detectable and/or otherwise hacker-prone encryption keys that are determined before in-body device installation and, instead, require inputs that can only be acquired from in-body characteristics.

The following examples identify additional example methods, apparatus, systems and/or articles of manufacture disclosed herein. An example apparatus to authorize a candidate medical device to communicate with an in-body network includes a device capability manager to identify remote sensors associated with the candidate medical device, an encryption engine to provide the candidate medical device with hashing instructions to be applied to input values from selected ones of the remote sensors, a measurement engine to acquire input values from local sensors corresponding to the selected ones of the available remote sensors during a measurement schedule, the encryption engine to apply the hashing instructions to the input values from the local sensors, and a pairing engine to authorize the candidate medical device when an encryption key associated with the remote sensors exhibits a threshold indication of parity with an encryption key associated with the local sensors. Other disclosed apparatus include a time stamp synchronizer to verify same time stamp values between input values from the selected ones of the remote sensors and the local sensors, in which the pairing engine is to prohibit the candidate medical device from communicating with the in-body network when the time stamp values associated with input values from the selected ones of the remote sensors differ from the time stamp values from the local sensors. Still other examples include a pairing engine to identify physiological effects of the in-body network and/or in other disclosed examples, the pairing engine is to verify the candidate medical device is inside a host, and a pattern engine is to compare a first set of remote sensor input values to a second set of remote sensor input values to verify the candidate medical device is inside the host. In still other disclosed examples, the apparatus includes a pattern engine to compare a rate of change of a first set of remote sensor input values to a second set of remote sensor input values to identify responses indicative of physiological effects of the host, in which responses indicative of physiological effects of the host comprise a threshold blood flow velocity change in response to a threshold heart rate change.

Example methods to authorize a candidate medical device to communicate with an in-body network include identifying remote sensors associated with the candidate medical device, providing the candidate medical device with hashing instructions to be applied to input values from selected ones of the remote sensors, acquiring input values from local sensors corresponding to the selected ones of the available remote sensors during a measurement schedule, applying the hashing instructions to the input values from the local sensors, and authorizing the candidate medical device when an encryption key associated with the remote sensors exhibits a threshold indication of parity with an encryption key associated with the local sensors. Some example methods include verifying same time stamp values between input values from the selected ones of the remote sensors and the local sensors, and prohibiting the candidate medical device from communicating with the in-body network when the time stamp values associated with input values from the selected ones of the remote sensors differ from the time stamp values from the local sensors. Other example methods include verifying the candidate medical device is inside a host, and comparing a first set of remote sensor input values to a second set of remote sensor input values to verify the candidate medical device is inside the host. Other example methods include comparing a rate of change of a first set of remote sensor input values to a second set of remote sensor input values to identify responses indicative of physiological effects of the host, and identifying responses indicative of physiological effects of the host based on a threshold blood flow velocity change in response to a threshold heart rate change.

An example disclosed computer readable storage medium includes instructions that, when executed, identify remote sensors associated with a candidate medical device, provide the candidate medical device with hashing instructions to be applied to input values from selected ones of the remote sensors, acquire input values from local sensors corresponding to the selected ones of the available remote sensors during a measurement schedule, apply the hashing instructions to the input values from the local sensors, and authorize the candidate medical device when an encryption key associated with the remote sensors exhibits a threshold indication of parity with an encryption key associated with the local sensors.

Some example disclosed instructions include verifying same time stamp values between input values from the selected ones of the remote sensors and the local sensors, while other example instructions include prohibiting the candidate medical device from communicating with the in-body network when the time stamp values associated with input values from the selected ones of the remote sensors differ from the time stamp values from the local sensors. Other example instructions include verifying the candidate medical device is inside a host, and comparing a first set of remote sensor input values to a second set of remote sensor input values to verify the candidate medical device is inside the host. Still other example instructions include comparing a rate of change of a first set of remote sensor input values to a second set of remote sensor input values to identify responses indicative of physiological effects of the host, and identifying responses indicative of physiological effects of the host based on a threshold blood flow velocity change in response to a threshold heart rate change.

Example systems to authorize a candidate medical device to communicate with an in-body network include means for identifying remote sensors associated with the candidate medical device, means for providing the candidate medical device with hashing instructions to be applied to input values from selected ones of the remote sensors, means for acquiring input values from local sensors corresponding to the selected ones of the available remote sensors during a measurement schedule, means for applying the hashing instructions to the input values from the local sensors, and means for authorizing the candidate medical device when an encryption key associated with the remote sensors exhibits a threshold indication of parity with an encryption key associated with the local sensors. Some example systems include means for verifying same time stamp values between input values from the selected ones of the remote sensors and the local sensors, and means for prohibiting the candidate medical device from communicating with the in-body network when the time stamp values associated with input values from the selected ones of the remote sensors differ from the time stamp values from the local sensors. Still other example systems include means for verifying the candidate medical device is inside a host, and means for comparing a first set of remote sensor input values to a second set of remote sensor input values to verify the candidate medical device is inside the host. Some example systems include means for comparing a rate of change of a first set of remote sensor input values to a second set of remote sensor input values to identify responses indicative of physiological effects of the host, and means for identifying responses indicative of physiological effects of the host based on a threshold blood flow velocity change in response to a threshold heart rate change.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus to authorize a candidate medical device to communicate with an in-body network, the apparatus comprising:
   a device capability manager to identify remote sensors associated with the candidate medical device;
   an encryption engine to provide the candidate medical device with hashing instructions to be applied to first input values acquired from selected ones of the remote sensors;
   a measurement engine to acquire second input values during a measurement schedule from local sensors embedded in a body hosting the in-body network, the local sensors corresponding to the selected ones of the remote sensors, the encryption engine to apply the hashing instructions to the second input values; and
   a pairing engine to authorize the candidate medical device to communicate with the in-body network when a first encryption key associated with the selected ones of the remote sensors and the hashing instructions exhibits a threshold indication of parity with a second encryption key associated with the corresponding ones of the local sensors and the hashing instructions, the first and second encryption keys generated in response to the selected ones of the remote sensors being embedded in the body.

2. An apparatus as defined in claim 1, further including a time stamp synchronizer to verify same time stamp values between the first and second input values.

3. An apparatus as defined in claim 2, wherein the pairing engine is to prohibit the candidate medical device from communicating with the in-body network when the time stamp values associated with the first input values differ from the time stamp values associated with the second input values.

4. An apparatus as defined in claim 1, wherein the pairing engine is to verify the candidate medical device is embedded in the body.

5. An apparatus as defined in claim 4, further including a pattern engine to compare a first set of the first input values to a second set of the first input values to verify the candidate medical device is embedded in the body.

6. An apparatus as defined in claim 4, further including a pattern engine to compare a rate of change of a first set of the first input values to a second set of the first input values to identify responses indicative of physiological effects of the body.

7. An apparatus as defined in claim 6, wherein responses indicative of physiological effects of the body include a threshold blood flow velocity change in response to a threshold heart rate change.

8. A method to authorize a candidate medical device to communicate with an in-body network, the method comprising:
   identifying remote sensors associated with the candidate medical device;
   providing the candidate medical device with hashing instructions to be applied to first input values acquired from selected ones of the remote sensors;
   acquiring second input values during a measurement schedule from local sensors embedded in a body hosting the in-body network, the local sensors corresponding to the selected ones of the remote sensors;
   applying the hashing instructions to the second input values; and
   authorizing the candidate medical device to communicate with the in-body network when a first encryption key associated with the selected ones of the remote sensors and the hashing instructions exhibits a threshold indication of parity with a second encryption key associated with the corresponding ones of the local sensors and the hashing instructions, the first and second encryption keys generated in response to the remote sensors being embedded in the body.

9. A method as defined in claim 8, further including verifying same time stamp values between the first and second input values.

10. A method as defined in claim 9, further including prohibiting the candidate medical device from communicating with the in-body network when the time stamp values associated with the first input values differ from the time stamp values associated with the second input values.

11. A method as defined in claim 8, further including verifying the candidate medical device is embedded in the body.

12. A method as defined in claim 11, further including comparing a first set of the first input values to a second set of the first input values to verify the candidate medical device is embedded in the body.

13. A method as defined in claim 11, further including comparing a rate of change of a first set of the first input values to a second set of the first input values to identify responses indicative of physiological effects of the body.

14. A method as defined in claim 13, further including identifying responses indicative of physiological effects of the body based on a threshold blood flow velocity change in response to a threshold heart rate change.

15. A machine accessible storage medium comprising instructions stored thereon that, when executed, cause a machine to at least:
   identify remote sensors associated with a candidate medical device;
   provide the candidate medical device with hashing instructions to be applied to first input values acquired from selected ones of the remote sensors;
   acquire second input values during a measurement schedule from local sensors embedded in a body hosting an in-body network, the local sensors corresponding to the selected ones of the remote sensors;
   apply the hashing instructions to the second input values; and
   authorize the candidate medical device to communicate with the in-body network when a first encryption key associated with the selected ones of the remote sensors and the hashing instructions exhibits a threshold indication of parity with a second encryption key associated with the corresponding ones of the local sensors and the hashing instructions, the first and second encryption keys generated in response to the remote sensors being embedded in the body.

16. A machine accessible storage medium as defined in claim 15, further including instructions that, when executed, cause the machine to verify same time stamp values between the first and second input values.

17. A machine accessible storage medium as defined in claim 16, further including instructions that, when executed, cause the machine to prohibit the candidate medical device from communicating with the in-body network when the time stamp values associated with the first input values differ from the time stamp values associated with the second input values.

18. A machine accessible storage medium as defined in claim 15, further including instructions that, when executed, cause the machine to verify the candidate medical device is embedded in the body.

19. A machine accessible storage medium as defined in claim 18, further including instructions that, when executed, cause the machine to compare a first set of the first input values to a second set of the first input values to verify the candidate medical device is embedded in the body.

20. A machine accessible storage medium as defined in claim 18, further including instructions that, when executed, cause the machine to compare a rate of change of a first set of the first input values to a second set of the first input values to identify responses indicative of physiological effects of the body.

* * * * *